(12) United States Patent
MacNeil et al.

(10) Patent No.: US 7,029,865 B2
(45) Date of Patent: Apr. 18, 2006

(54) DNA MOLECULES ENCODING THE MELANOCORTIN 4 RECEPTOR PROTEIN FROM RHESUS MONKEY

(75) Inventors: Douglas J. MacNeil, Westfield, NJ (US); David H. Weinberg, Westfield, NJ (US); Leonardus H. T. Van Der Ploeg, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 341 days.

(21) Appl. No.: 10/373,355

(22) Filed: Feb. 25, 2003

(65) Prior Publication Data

US 2003/0166009 A1    Sep. 4, 2003

Related U.S. Application Data

(62) Division of application No. 09/831,206, filed as application No. PCT/US99/25767 on Nov. 5, 1999, now Pat. No. 6,573,070.

(60) Provisional application No. 60/107,721, filed on Nov. 9, 1998.

(51) Int. Cl.
 G01N 33/567   (2006.01)
 C07K 1/00     (2006.01)
 C07H 21/04    (2006.01)
 C12N 1/20     (2006.01)
 C12P 21/02    (2006.01)

(52) U.S. Cl. .................. 435/7.21; 435/69.5; 435/252.3; 435/320.1; 436/501; 514/2; 530/350; 530/388.22; 536/23.5

(58) Field of Classification Search ............... 435/7.21, 435/69.5, 252.3, 320.1; 436/501; 514/2; 530/350, 388.22; 536/23.5
 See application file for complete search history.

(56) References Cited

U.S. PATENT DOCUMENTS

| | | | |
|---|---|---|---|
| 5,280,112 A | 1/1994 | Cone et al. | |
| 5,532,347 A | 7/1996 | Cone et al. | |
| 5,622,860 A | 4/1997 | Yamada et al. | |
| 5,703,220 A * | 12/1997 | Yamada et al. | 536/23.5 |
| 5,710,265 A | 1/1998 | Yamada et al. | |

OTHER PUBLICATIONS

Offermanns-S, et al., J. Biol. Chem. 270(25)1575-1580, 1995.*

Guo-HH et al. PNAS 101(25)9205-9210, 2004.*
Bowie et al., 1990, Science 247:1306-1310.*
Gantz, I. et al. "Molecular Cloning, Expression, and Gene Localization of a Fourth Melanocortin Receptor", J. of Biol. Chem., 1993, vol. 268, pp. 15174-15179.
Koegler, F. et al. "Central Melanocortin Receptors Mediate Changes in Food Intake in the Rhesus Macaque", Endocrinology, 2001, vol. 142, pp. 2586-2592.
Mountjoy, K. et al. "The Cloning of a Family of Genes That Encode the Melanocortin Receptors", Science, 1992, vol. 257, pp. 1248-1251.
Chhajlani, V. et al. "Molecular cloning and expression of the human melanocyte stimulating hormone receptor cDNA", FEBS Letters, 1992, vol. 309, pp. 417-420.
Roselli-Rehfuss, L. et al. "Identification of a receptor for y melanotropin and other proopiomelanocortin peptides in the hypothalamus and limbic system", Proc. Natl. Acad. Sci. USA, 1993, vol. 90, pp. 8856-8860.
Gantz, I. et al. "Molecular Cloning of a Novel Melanocortin Receptor", J. of Biol. Chem. 1993, vol. 268, pp. 8246-8250.
Mountjoy, K. et al. "Localization of the Melanocortin-4 Receptor (MC4-R) in Neuroendocrine and Autonomic Control Circuits in the Brain", Molecular Endocrinology, 1994, vol. 8, pp. 1298-1308.
Chhajlani, V. et al. "Molecular Cloning of a Novel Human Nelanocortin Receptor", Biochemical and Biophysical Research Communications, 1993, vol. 195, pp. 866-873.
Fathi, Z. et al. "Cloning, Expression, and Tissue Distribution of a Fifth Melanocortin Receptor Subtype", Neurochemical Research, 1995, vol.20, pp. 107-113.
Griffon, N. et al. "Molecular Cloning and Characterization of the Rat Fifth Melanocortin Receptor", Biochemical and Biophysical Research Communications, 1994, vol. 200, pp. 1007-1014.

(Continued)

Primary Examiner—Elizabeth Kemmerer
Assistant Examiner—Michael Brannock
(74) Attorney, Agent, or Firm—Alysia A. Finnegan; Joanne M. Giesser

(57) ABSTRACT

The present invention relates to rhesus monkey DNA molecules encoding the melanocortin-4 receptor protein, recombinant vectors comprising DNA molecules encoding rhesus MC-4R, recombinant host cells which contain a recombinant vectors encoding rhesus MC-4R, the rhesus MC-4R protein encoded by the DNA molecule, and methods of identifying selective agonists and antagonists of rhesus MC-4R.

4 Claims, 3 Drawing Sheets

OTHER PUBLICATIONS

Gantz, I. et al. "Molecular Cloning, Expression, and Characterization of a Fifth Melanocortin Receptor", Biochemical and Biophysical Research Communications, 1994, vol. 200, pp. 1214-1220.

Labbe, O. et al. "Molecular Cloning of a Mouse Melanocortin 5 Receptor Gene Widely Expressed in Peripheral Tissues", Biochemistry, 1994, vol. 33, pp. 4543-4549.

Barrett, P. et al. "Cloning and expression of a new member of the melanocyte-stimulating hormone receptor family", J. of Mol. Endocrin., 1994, vol. 12, pp. 203-213.

Fan, W. et al. "Role of melanocortinergic neurons in feeding and the agouti obesity syndrome", Nature, 1997, vol. 385, pp. 165-168.

Huszar, D. et al. "Targeted Disruption of the Melanocortin-4 Receptor Results in Obesity in Mice", Cell, 1997, vol. 88, pp. 131-141.

Fong, T. et al. "Molecular Basis for the Species Selectively of the Neurokinin-1 Receptor Antagonists CP-96,345 and RP67580", J. of Biol. Chem., 1992, vol. 267, pp. 25668-25671.

Hartig, P. et al. "A subfamily of 5-HT 1D receptor genes", TIPS, 1992, vol. 13, pp. 152-159.

* cited by examiner

GAATTCTCCTGCCAGCATGGTGAACTCCACCCACCGTGGGATGCACGCTTCTCTGCACCT 60
            M  V  N  S  T  H  R  G  M  H  A  S  L  H  L

CTGGAACCGCAGCAGCCACAGACTGCACAGCAATGCCAGTGAGTCCCTTGGAAAAGGCTA 120
 W  N  R  S  S  H  R  L  H  S  N  A  S  E  S  L  G  K  G  Y

CTCTGATGGAGGGTGCTACGAGCAACTTTTTGTCTCTCCTGAGGTGTTTGTGACACTGGG 180
 S  D  G  G  C  Y  E  Q  L  F  V  S  P  E  V  F  V  T  L  G

TGTCATCAGCTTGTTGGAGAATATCTTAGTGATTGTGGCAATAGCCAAGAACAAGAATCT 240
 V  I  S  L  L  E  N  I  L  V  I  V  A  I  A  K  N  K  N  L

GCATTCACCCATGTACTTTTTCATCTGCAGCCTGGCTGTGGCTGATATGCTGGTGAGCGT 300
 H  S  P  M  Y  F  F  I  C  S  L  A  V  A  D  M  L  V  S  V

TTCAAATGGATCAGAAACCATTGTCATCACCCTATTAAACAGTACAGATACGGACACACA 360
 S  N  G  S  E  T  I  V  I  T  L  L  N  S  T  D  T  D  T  Q

GAGTTTCACAGTGAACATTGATAATGTTATTGACTCAGTGATCTGTAGCTCCTTGCTTGC 420
 S  F  T  V  N  I  D  N  V  I  D  S  V  I  C  S  S  L  L  A

ATCCATTTGCAGCCTGCTTTCAATTGCAGTGGACAGGTACTTTACTATCTTCTATGCTCT 480
 S  I  C  S  L  L  S  I  A  V  D  R  Y  F  T  I  F  Y  A  L

TCAGTACCATAACATTATGACAGTTAAGCGGGTTGGGATCATCATAAGTTGTATCTGGGC 540
 Q  Y  H  N  I  M  T  V  K  R  V  G  I  I  I  S  C  I  W  A

AGCTTGCACGGTTTCAGGCATTTTGTTCATCATTTACTCAGATAGTAGTGCTGTCATCAT 600
 A  C  T  V  S  G  I  L  F  I  I  Y  S  D  S  S  A  V  I  I

CTGCCTCATCACCATGTTCTTCACCATGTTGGCTCTCATGGCTTCTCTCTATGTCCACAT 660
 C  L  I  T  M  F  F  T  M  L  A  L  M  A  S  L  Y  V  H  M

GTTCCTGATGGCCAGGCTTCACATTAAGAGGATTGCTGTCCTCCCCGGCACTGGTGCCAT 720
 F  L  M  A  R  L  H  I  K  R  I  A  V  L  P  G  T  G  A  I

CCGCCAAGGCGCCAATATGAAGGGAGCGATTACTTTGACCATCCTGATTGGCGTCTTTGT 780
 R  Q  G  A  N  M  K  G  A  I  T  L  T  I  L  I  G  V  F  V

TGTCTGCTGGGCCCCATTCTTCCTCCACTTAATATTCTACATCTCTTGTCCTCAGAATCC 840
 V  C  W  A  P  F  F  L  H  L  I  F  Y  I  S  C  P  Q  N  P

FIG.1A

```
ATATTGTGTGTGCTTCATGTCTCACTTTAACTTGTATCTCATACTGATCATGTGTAATTC    900
 Y  C  V  C  F  M  S  H  F  N  L  Y  L  I  L  I  M  C  N  S

AGTCATCGATCCTCTGATTTATGCACTCCGGAGTCAAGAACTAAGGAAAACCTTCAAAGA    960
 V  I  D  P  L  I  Y  A  L  R  S  Q  E  L  R  K  T  F  K  E

GATCATCTGTTGCTATCCCCTGGGAGGCCTATGTGACTTGTCTAGCAGATATTAAATGGG   1020
 I  I  C  C  Y  P  L  G  G  L  C  D  L  S  S  R  Y  *  (SEQ ID NO:2)

GACAGAGCAC (SEQ ID NO:1)
```

FIG. 1B

```
  1 MVNSTHRGMH ASLHLWNRSS HRLHSNASES LGKGYSDGGC YEQLFVSPEV

51 FVTLGVISLL ENILVIVAIA KNKNLHSPMY FFICSLAVAD MLVSVSNGSE

101 TIVITLLNST DTDTQSFTVN IDNVIDSVIC SSLLASICSL LSIAVDRYFT

151 IFYALQYHNI MTVKRVGIII SCIWAACTVS GILFIIYSDS SAVIICLITM

201 FFTMLALMAS LYVHMFLMAR LHIKRIAVLP GTGAIRQGAN MKGAITLTIL

251 IGVFVVCWAP FFLHLIFYIS CPQNPYCVCF MSHFNLYLIL IMCNSVIDPL

301 IYALRSQELR KTFKEIICCY PLGGLCDLSS RY (SEQ ID NO:2)
```

FIG.2

DNA MOLECULES ENCODING THE MELANOCORTIN 4 RECEPTOR PROTEIN FROM RHESUS MONKEY

CROSS-REFERENCE TO RELATED APPLICATIONS

This application is a divisional of U.S. Ser. No. 09/831,206, filed May 4, 2001, now U.S. Pat. No. 6,573,070 which is a 371 of PCT/US99/25767, international filing date of Nov. 5, 1999, which claims priority to U.S. Ser. No. 60/107,721, filed Nov. 9, 1998, now abandoned.

FIELD OF THE INVENTION

The present invention relates to rhesus monkey (*Macaca mulatta*) DNA molecules encoding the melanocortin-4 receptor protein belonging to the rhodopsin sub-family of G-protein coupled receptors, recombinant vectors comprising DNA molecules encoding rhesus MC-4R, recombinant host cells which contain a recombinant vector encoding rhesus MC-4R, the rhesus MC-4R protein encoded by the DNA molecule, and methods of identifying selective agonists and antagonists of rhesus MC-4R.

BACKGROUND OF THE INVENTION

Melanocortin receptors belong to the rhodopsin sub-family of G-protein coupled receptors (GPCRs). Five different subtypes are known. These melanocortin receptors bind and are activated by peptides such as α-, β, or γ-melanocyte stimulating hormones (α-, β-, γ-MSH) derived from the pro-opiomelanocortin (POMC) gene. A wide range of physiological functions are believed to be mediated by melanocortin peptides and their receptors.

U.S. Pat. No. 5,532,347 (issued Jul. 2, 1996) to Cone and Mountjoy discloses human and mouse DNA molecules which encode MC-1R (also known in the art as α-MSH-R). The expressed human protein contains 317 amino acids.

U.S. Pat. No. 5,280,112 (issued Jan. 18, 1994) and U.S. Pat. No. 5,554,729 (issued Sep. 10, 1996), both to Cone and Mountjoy, disclose human and mouse DNA molecules which encode MC-2R (also known in the art as ACTH-R). The human MC-2R protein contains 297 amino acids.

Mountjoy, et al. (1992, *Science* 257: 1248–1251) describe DNA molecules and the concomitant protein for human MC-1R and human MC-2R.

Chhajlani, et al. (1992, *FEBS Letters* 309: 417–420) also disclose a human DNA molecule comprising an open reading frame which encodes human MC1-R.

Roselli-Rehfuss, et al, (1993, *Proc. Natl. Acad. Sci* 90: 8856–8860) disclose a cDNA clone encoding rat MC-3R cDNA.

U.S. Pat. No. 5,622,860 (issued Apr. 22, 1997) and U.S. Pat. No. 5,703,220 (issued Dec. 30, 1997) to Yamada and Gantz, disclose DNA molecules which encode human MC-3R and human MC-4R, respectively (see also Gantz, et al., 1993, *J. Biol. Chem.* 268(11): 8246–8250).

A DNA molecule encoding human MC-5R was also disclosed by Mountjoy, et al. (1994, *Mol. Endocrin.* 8: 1298–1308).

Chhajlani, et al. (1993, *Biochem. Biophys. Res. Comm.,* 195(2): 866–873) disclose a DNA molecule which the authors state encodes MC-5R. This clone was initially designated MC2.

Fathi, et al. (1995, *Neurochemical Research* 20(1):107–113) also disclose a DNA molecule thought to encode human MC-5R. There are several sequence discrepancies when compared to the DNA molecule disclosed by Chhajlani, et al., id.

Griffon, et al. (1994, *Biochem. Biophys. Res. Comm.,* 200(2): 1007–1014) disclose DNA clones from human and rat which encode MC-5R. The human DNA sequence agrees with the human DNA sequence disclosed in Fathi et al. id.

Gantz, et al. (1994, *Biochem. Biophys. Res. Comm.,* 200(3): 11214–11220; see also U.S. Pat. No. 5,710,265, issued Jan. 20, 1998 to Yamada and Gantz) and Labbe, et al. (1994, *Biochemistry* 33: 4543–4549) disclose DNA clones from mouse which encode MC-5R.

Barrett, et al. (1994, *J. Mol. Endocrin.* 12: 203–213) disclose DNA clones from sheep which encode MC-5R.

In rodents, MC-4R has been implicated as a key regulator of feeding behavior which regulates body weight through studies with peptide agonists and antagonists (Fan et al., 1997, *Nature* 385: 165–168) and with a MC-4R knock-out mouse (Huszar et al., 1997, *Cell* 88: 131–141).

Compounds that bind to such receptors were previously identified by binding to human and/or rodent receptors and evaluated for their efficacy in rodents. However, the neuroendocrine process can differ between rodents and man. It is also expected that some compounds exhibit different binding affinities for different species homologues of the same receptor (Fong et al., 1992, *J.Biol. Chem.* 267:25666–25671; Hartig et al., 1992, *TIPS* 13:152–159).

Before compounds can be selected as a drug candidate it is first evaluated for a physiological effect in rodents and then in the rhesus primate. It is often that one compound may be effective in one animal species but not in another. Previously, it has been impossible to determine if the failure was due to an altered melanocortin pathway in different species, or due to a compounds having a lower affinity for one particular species. Past protocols required the use of a rhesus brain membrane to determine the in vitro biochemical activity of compounds, if such protocol could be successfully employed.

It is desirable to correlate in vivo data with in vitro biochemical activity of compounds.

It is also desirable to first select compounds that are active for the rhesus receptor in vitro.

It is also desirable to identify compounds which can determine the relevance of receptor targets in rhesus and allow selection of novel drugs to treat obesity.

It is further desirable to discover new drugs which effect pathophysiological processes by modulating the effects in rhesus to identify melanocortin active process in primates, followed by human clinical trials.

The present invention addresses and meets these needs by disclosing an isolated nucleic acid fragment which expresses a form of rhesus MC-4R, recombinant vectors which house this nucleic acid fragment, recombinant host cells which expresses rhesus MC-4R and/or a biologically active equivalent, and pharmacological properties of this rhesus MC-4R protein.

SUMMARY OF THE INVENTION

The present invention relates to an isolated nucleic acid molecule (polynucleotide) which encodes a novel rhesus monkey (*Macaca mulatta*) melanocortin-4 receptor (rhMC-4R). The nucleic acid molecules of the present invention are substantially free from other nucleic acids.

The present invention relates to an isolated nucleic acid molecule (polynucleotide) which encodes mRNA which expresses a novel rhesus MC-4R, this DNA molecule comprising the nucleotide sequence disclosed herein as SEQ ID NO:1.

The present invention also relates to biologically active fragments or mutants of SEQ ID NO:1 which encodes mRNA expressing a novel rhesus MC-4R. Any such biologically active fragment and/or mutant will encode either a protein or protein fragment which at least substantially mimics the pharmacological properties of a wild-type MC-4R protein, including but not limited to the rhesus MC-4R receptor protein as set forth in SEQ ID NO:2. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for MC-4R function.

A preferred aspect of this portion of the present invention is disclosed in FIG. 1, a rhesus cDNA molecule encoding a novel MC-4R (SEQ ID NO:1).

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification.

The present invention also relates to subcellular membrane fractions of the recombinant host cells (both prokaryotic and eukaryotic as well as both stably and transiently transformed cells) which contain the proteins encoded by the nucleic acids of the present invention. These subcellular membrane fractions will comprise either wild-type or mutant forms of rhesus melanocortin-4 receptor proteins at levels substantially above endogenous levels and hence will be useful in various assays to select modulators of rhesus melanocortin-4 receptor protein as described throughout this specification.

The present invention also relates to a substantially purified form of the rhesus melanocortin-4 receptor protein, which comprises the amino acid sequence disclosed in FIG. 2 and set forth as SEQ ID NO:2. A preferred aspect of the present invention is disclosed in FIG. 2 and is set forth as SEQ ID NO:2, the amino acid sequence of the novel rhesus melanocortin-4 receptor protein.

The present invention also relates to biologically active fragments and/or mutants of the rhesus melanocortin-4 receptor protein comprising the amino acid sequence set forth as SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists for MC-4R function.

The present invention also relates to assays to screen or select for various modulators of MC-4R activity, methods of expressing the MC-4R protein and biological equivalents disclosed herein, recombinant host cells which comprise DNA constructs which express these receptor proteins, and compounds identified through these assays which act as agonists or antagonists of MC-4R activity.

The present invention also relates to isolated nucleic acid molecules which are fusion constructions expressing fusion proteins useful in assays to identify compounds which modulate wild-type vertebrate MC-4R activity. A preferred aspect of this portion of the invention includes, but is not limited to, glutathione S-transferase (GST)-MC-4R fusion constructs which include, but are not limited to, either the intracellular domain of rhesus MC-4R as an in-frame fusion at the carboxy terminus of the GST gene, or the extracellular and transmembrane ligand binding domain of MC-4R fused to the amino terminus of GST, or the extracellular and transmembrane domain of MC-4R fused to an immunoglobulin gene by methods known to one of ordinary skill in the art. Soluble recombinant GST-MC-4R fusion proteins may be expressed in various expression systems, including *Spodoptera frugiperda* (Sf21) insect cells (Invitrogen) using a baculovirus expression vector (pAcG2T, Pharmingen).

Therefore, the present invention relates to methods of expressing the rhesus MC-4R protein and biological equivalents disclosed herein, assays employing these gene products, recombinant host cells which comprise DNA constructs which express these receptor proteins, and compounds identified through these assays which act as agonists or antagonists of MC-4R activity.

The present invention also relates to polyclonal and monoclonal antibodies raised in response to either the rhesus form of MC-4R, or a biologically active fragment thereof.

It is an object of the present invention to provide an isolated nucleic acid molecule which encodes a novel form of rhesus MC-4R, or rhesus fragments MC-4R fragments, mutants or derivatives of SEQ ID NO:2. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for vertebrate MC-4R function.

It is a further object of the present invention to provide the rhesus MC-4R proteins or protein fragments encoded by the nucleic acid molecules referred to in the preceding paragraph.

It is a further object of the present invention to provide recombinant vectors and recombinant host cells which comprise a nucleic acid sequence encoding rhesus MC-4R or a biological equivalent thereof.

It is an object of the present invention to provide a substantially purified form of the rhesus MC-4R protein, as set forth in SEQ ID NO:2.

It is an object of the present invention to provide for biologically active fragments and/or mutants of the rhesus MC-4R protein, such as set forth in SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use.

It is also an object of the present invention to provide for MC-4R-based assays to select for modulators of this receptor protein. These assays are preferably cell based assays whereby a DNA molecule encoding MC-4R is transfected or transformed into a host cell, this recombinant host cell is allowed to grow for a time sufficient to express MC-4R prior to use in various assays described herein.

It is a further object to provide for membrane preparations from host cells transfected or transformed with a DNA molecule encoding MC-4R for use in assays to select for modulators of MC-4R activity.

It is also an object of the present invention to provide for MC-4R-based in-frame fusion constructions, methods of expressing these fusion constructs, biological equivalents disclosed herein, related assays, recombinant cells expressing these constructs, and agonistic and/or antagonistic compounds identified through the use of the nucleic acid encoding vertebrate MC-4R protein as well as the expressed protein.

As used herein, "rh" or refers to—rhesus—.

As used herein, "MC-4R" refers to—melanocortin 4 receptor—.

As used herein, "GPCR" refers to—G-protein coupled receptor—.

Whenever used herein, the term "mammalian host" will refer to any mammal, including a human being.

BRIEF DECRIPTION OF THE FIGURES

FIG. 1A and FIG. 1B show the nucleotide sequence which encodes rhesus MC-4R, as set forth in SEQ ID NO:1.

FIG. 2 shows the one-letter designation of the amino acid sequence of rhesus MC-4R, as also set forth in SEQ ID NO:2 as a three letter designation.

DETAILED DESCRIPTION OF THE INVENTION

The present invention relates to an isolated nucleic acid molecule (polynucleotide) which encodes a novel rhesus monkey (*Macaca mulatta*) melanocortin-4 receptor (rhMC-4R). The nucleic acid molecules of the present invention are substantially free from other nucleic acids. For most cloning purposes, DNA is a preferred nucleic acid.

The present invention relates to an isolated nucleic acid molecule (polynucleotide) which encodes mRNA which expresses a novel rhesus MC-4R, this DNA molecule comprising the nucleotide sequence disclosed herein as SEQ ID NO:1, shown herein as follows:

```
GAATTCTCCT GCCAGCATGG TGAACTCCAC CCACCGTCGG ATGCACGCTT CTCTGCACCT  (SEQ ID NO:1)

CTGGAACCGC AGCAGCCACA GACTGCACAG CAATGCCAGT GAGTCCCTTG GAAAAGGCTA

CTCTGATGGA GGGTGCTACG AGCAACTTTT TGTCTCTCCT GAGGTGTTTG TGACACTGGG

TGTCATCAGC TTGTTGGAGA ATATCTTAGT GATTGTGGCA ATAGCCAAGA ACAAGAATCT

GCATTCACCC ATGTACTTTT TCATCTGCAG CCTGGCTGTG GCTGATATGC TGGTGAGCGT

TTCAAATGGA TCAGAAACCA TTGTCATCAC CCTATTAAAC AGTACAGATA CGGACACACA

GAGTTTCACA GTGAACATTG ATAATGTTAT TGACTCAGTG ATCTGTAGCT CCTTGCTTGC

ATCCATTTGC AGCCTGCTTT CAATTGCAGT GGACACGTAC TTTACTATCT TCTATGCTCT

TCAGTACCAT AACATTATGA CAGTTAAGCG GGTTGGGATC ATCATAAGTT GTATCTCGGC

AGCTTGCACG GTTTCAGGCA TTTTGTTCAT CATTTACTCA GATAGTAGTG CTGTCATCAT

CTGCCTCATC ACCATCTTCT TCACCATGTT GGCTCTCATG GCTTCTCTCT ATGTCCACAT

GTTCCTGATG GCCAGGCTTC ACATTAAGAG GATTGCTGTC CTCCCCGGCA CTGGTGCCAT

CCGCCAAGGC GCCAATATGA AGGGAGCGAT TACTTTGACC ATCCTGATTG GCGTCTTTGT

TGTCTGCTGG GCCCCATTCT TCCTCCACTT AATATTCTAC ATCTCTTGTC CTCAGAATCC

ATATTGTGTG TGCTTCATGT CTCACTTTAA CTTGTATCTC ATACTGATCA TGTGTAATTC

AGTCATCGAT CCTCTGATTT ATGCACTCCG GAGTCAAGAA CTAAGGAAAA CCTTCAAAGA

GATCATCTGT TGCTATCCCC TGGGAGGCCT ATGTGACTTG TCTAGCAGAT ATTAAATGGG

GACAGAGCAC.
```

The above-exemplified isolated DNA molecule, shown in FIG. 1 and set forth as SEQ ID NO:1, contains 1030 nucleotides. This DNA molecule contains an open reading frame from nucleotide 17 to nucleotide 1012, with a "TAA" termination codon at nucleotides 1013–1015. This open reading frame encodes a rhesus MC-4R protein 332 amino acids in length, as shown in FIG. 2 and as set forth in SEQ ID NO:2.

The present invention also relates to biologically active fragments or mutants of SEQ ID NO:1 which encodes mRNA expressing a novel rhesus MC-4R. Any such biologically active fragment and/or mutant will encode either a protein or protein fragment which at least substantially mimics the pharmacological properties of a wild-type MC-4R protein, including but not limited to the rhesus MC-4R receptor protein as set forth in SEQ ID NO:2. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for MC-4R function.

A preferred aspect of this portion of the present invention is disclosed in FIG. 1, a rhesus cDNA molecule encoding a novel MC-4R (SEQ ID NO:1).

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

It is known that there is a substantial amount of redundancy in the various codons which code for specific amino acids. Therefore, this invention is also directed to those DNA sequences encode RNA comprising alternative codons which code for the eventual translation of the identical amino acid, as shown below:

```
A = Ala = Alanine
codons GCA, GCC, GCG, GCU

C = Cys = Cysteine
codons UGC, UGU

D = Asp = Aspartic acid
codons GAC, GAU

E = Glu = Glutamic acid
codons GAA, GAG

F = Phe = Phenylalanine
codons UUC, UUU

G = Gly = Glycine
codons GGA, GGC, GGG, GGU

H = His = Histidine
codons CAC, CAU

I = Ile = Lsoleucine
codons AUA, AUC, AUU

K = Lys = Lysine
codons AAA, AAG

L = Leu = Leucine
codons UUA, UUG, CUA, CUC, CUG, CUU

M = Met = Methionine
codon  AUG

N = Asp = Asparagine
codons AAC, AAU

P = Pro = Proline
codons CCA, CCC, CCG, CCU

Q = Gln = Glutamine
codons CAA, CAG

R = Arg = Arginine
codons AGA, AGG, CGA, CGC, CGG, CGU

S = Ser = Serine
codons AGC, AGU, UCA, UCC, UCG, UCU

T = Thr = Threonine
codons ACA, ACC, ACG, ACU

V = Val = Valine
codons GUA, GUC, GUG, GUU

W = Trp = Tryptophan
codon  UGG

Y = Tyr = Tyrosine
codons UAC, UAU
```

Therefore, the present invention discloses codon redundancy which may result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

Included in the present invention are DNA sequences that hybridize to SEQ ID NO:1 under stringent conditions. By way of example, and not limitation, a procedure using conditions of high stringency is as follows: Prehybridization of filters containing DNA is carried out for 2 hours to overnight at 65° C. in buffer composed of 6×SSC, 5×Denhardtís solution, and 100 µg/ml denatured salmon sperm DNA. Filters are hybridized for 12 to 48 hrs at 65° C. in prehybridization mixture containing 100 µg/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5×Denhardtís solution, 50% formamide at 42° C. for 12 to 48 hours or a washing step carried out in 0.2×SSPE, 0.2% SDS at 65° C. for 30 to 60 minutes.

The present invention also relates to isolated nucleic acid molecules which are fusion constructions expressing fusion proteins useful in assays to identify compounds which modulate wild-type vertebrate MC-4R activity. A preferred aspect of this portion of the invention includes, but is not limited to, glutathione S-transferase (GST)-MC-4R fusion constructs which include, but are not limited to, either the intracellular domain of rhesus MC-4R as an in-frame fusion at the carboxy terminus of the GST gene or the extracellular and transmembrane ligand binding domain of MC-4R fused to an GST or immunoglobulin gene by methods known to one of ordinary skill in the art. Recombinant GST-MC-4R fusion proteins may be expressed in various expression systems, including *Spodoptera frugiperda* (Sf21) insect cells (Invitrogen) using a baculovirus expression vector (pAcG2T, Pharmingen).

Any of a variety of procedures may be used to clone rhesus MC-4R. These methods include, but are not limited to, (1) a RACE PCR cloning technique (Frohman, et al., 1988, *Proc. Natl. Acad. Sci. USA* 85: 8998–9002). 5' and/or 3' RACE may be performed to generate a full-length cDNA sequence. This strategy involves using gene-specific oligonucleotide primers for PCR amplification of rhesus MC-4R cDNA. These gene-specific primers are designed through identification of an expressed sequence tag (EST) nucleotide sequence which has been identified by searching any number of publicly available nucleic acid and protein databases; (2) direct functional expression of the rhesus MC-4R cDNA following the construction of a rhesus MC-4R-containing cDNA library in an appropriate expression vector system; (3) screening a rhesus MC-4R-containing cDNA library constructed in a bacteriophage or plasmid shuttle vector with a labeled degenerate oligonucleotide probe designed from the amino acid sequence of the rhesus MC-4R protein; (4) screening a rhesus MC-4R-containing cDNA library constructed in a bacteriophage or plasmid shuttle vector with a partial cDNA encoding the rhesus MC-4R protein. This partial cDNA is obtained by the specific PCR amplification of rhesus MC-4R DNA fragments through the design of degenerate oligonucleotide primers from the amino acid sequence known for other kinases which are related to the rhesus MC-4R protein; (5) screening a rhesus MC-4R-containing cDNA library constructed in a bacteriophage or plasmid shuttle vector with a partial cDNA or oligonucleotide with homology to a mammalian MC-4R protein. This strategy may also involve using gene-specific oligonucleotide primers for PCR amplification of rhesus MC-4R cDNA identified as an EST as described above; or (6) designing 5' and 3' gene specific oligonucleotides using SEQ ID NO: 1 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding rhesus MC-4R.

It is readily apparent to those skilled in the art that other types of libraries, as well as libraries constructed from other cell types-or species types, may be useful for isolating a rhesus MC-4R-encoding DNA or a rhesus MC-4R homologue. Other types of libraries include, but are not limited to, cDNA libraries derived from other rhesus cells.

It is readily apparent to those skilled in the art that suitable cDNA libraries may be prepared from cells or cell lines which have MC-4R activity. The selection of cells or cell lines for use in preparing a cDNA library to isolate a cDNA encoding rhesus MC-4R may be done by first measuring cell-associated MC-4R activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual;* Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding rhesus MC-4R may also be isolated from a suitable genomic DNA library. Construction of genomic DNA libraries can be performed by standard techniques well known in the art. Well known genomic DNA library construction techniques can be found in Sambrook, et al., supra.

In order to clone the rhesus MC-4R gene by one of the preferred methods, the amino acid sequence or DNA sequence of rhesus MC-4R or a homologous protein may be necessary. To accomplish this, the MC-4R protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial rhesus MC-4R DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the rhesus MC-4R sequence but others in the set will be capable of hybridizing to rhesus MC-4R DNA even in the presence of DNA oligonucleotides with mismatches. The mismatched DNA oligonucleotides may still sufficiently hybridize to the rhesus MC-4R DNA to permit identification and isolation of rhesus MC-4R encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1, either for the purpose of isolating overlapping 5' and 3' RACE products for generation of a full-length sequence coding for rhesus MC-4R, or to isolate a portion of the nucleotide sequence coding for rhesus MC-4R for use as a probe to screen one or more cDNA-or genomic-based libraries to isolate a full-length sequence encoding rhesus MC-4R or rhesus MC-4R-like proteins.

Reagents mentioned in the foregoing procedures for carrying out high stringency hybridization are well known in the art. Details of the composition of these reagents can be found in, e.g., Sambrook et al., 1989, *Molecular Cloning: A Laboratory Manual;* Cold Spring Harbor Laboratory, Cold Spring Harbor, N.Y. In addition to the foregoing, other conditions of high stringency which may be used are well known in the art.

Melanocortin receptors belong to the rhodopsin sub-family of GPCRs. However, several features in the rhMC-4R are shared with all other receptors and are absent in most other GPCRs, including the EN motif in TM1, the lack of Cys in the loop between TM2 and TM3 or between TM4 and TM5, the MxxxxxxxY motif in TM5, and the DPxxY motif in TM7. Since all melanocortin receptors lack Cys residues in the extracellular loops that are present in other members of the rhodopsin sub-family, interhelical disulfide bond (e.g., between the Cys residues near the top of TM3 and TM5) may play the same function as interloop disulfide bond in most other GPCRs.

The present invention also relates to a substantially purified form of the rhesus melanocortin-4 receptor protein, which comprises the amino acid sequence is disclosed in FIG. 2 and set forth as SEQ ID NO:2.

A preferred aspect of the present invention is disclosed in FIG. 2 and is set forth as SEQ ID NO:2, and as herein set forth as follows:

MVNSTHRGMH ASLHLWNRSS HRLHSNASES LGKGYSDGGC YEQLFVSPEV FVTLGVISLL ENIL-VIVAIA KNKNLHSPMY FFICSLAVAD MLVSVSNGSE TIVITLLNST DTDTQSFTVN IDNVIDSVIC SSLLA-SICSL LSIAVDRYFT IFYALQYHNI MTVKRVGIII SCI-WAACTVS GILFIIYSDS SAVIICLITM FFTMLALMAS LYVHMFLMAR LHIKRIAVLP GTGAIRQGAN MKGAITLTIL IGVFVVCWAP FFLHLIFYIS CPQNPY-CVCF MSHFNLYLIL IMCNSVIDPL IYALRSQELR KTFKEIICCY PLGGLCDLSS RY (SEQ ID NO:2), which comprises the amino acid sequence of wild type rhesus melanocortin-4 receptor protein.

The present invention also relates to biologically active fragments and/or mutants of the rhesus melanocortin-4 receptor protein comprising the amino acid sequence set forth as SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists for MC-4R function.

As with many receptor proteins, it is possible to modify many of the amino acids, particularly those which are not found in the ligand binding domain, and still retain substantially the same biological activity as the original receptor. Thus this invention includes modified rhMC-R polypeptides which have amino acid deletions, additions, or substitutions but that still retain substantially the same biological activity as rhMC-4R. It is generally accepted that single amino acid substitutions do not usually alter the biological activity of a protein (see, e.g., *Molecular Biology of the Gene*, Watson et al., 1987, Fourth Ed., The Benjamin/Cummings Publishing Co., Inc., page 226; and Cunningham & Wells, 1989, *Science* 244:1081–1085). Accordingly, the present invention includes isolated nucleic acid molecules and expressed MC-4R proteins wherein one amino acid substitution is generated and which this protein retains substantially the same biological activity as wild-type rhMC-R. The present invention also includes isolated nucleic acid molecules and expressed MC-4R proteins wherein two or more amino acid substitution is generated wherein this protein retains substantially the same biological activity as wild-type rhMC-4R. In particular, the present invention includes embodiments where the above-described substitutions are conservative substitutions. In particular, the present invention includes embodiments where the above-described substitutions do not occur in the ligand-binding domain of rhMC-4R.

The present invention also relates to subcellular membrane fractions from the recombinant host cells (both prokaryotic and eukaryotic as well as both stably and transiently transformed cells) which contain the nucleic acids of the present invention. These subcellular membrane fractions will comprise either wild-type or mutant forms of rhesus melanocortin-4 receptor proteins at levels substantially above endogenous levels and hence will be useful in various assays described throughout this specification.

The present invention also relates to recombinant vectors and recombinant hosts, both prokaryotic and eukaryotic, which contain the substantially purified nucleic acid molecules disclosed throughout this specification. The nucleic acid molecules of the present invention encoding rhMC-R, in whole or in part, can be linked with other DNA molecules, i.e., DNA molecules to which the rhMC-4R are not naturally linked, to form recombinant DNA molecules containing the receptor. The novel DNA sequences of the present invention can be inserted into vectors which comprise nucleic acids encoding a rhMC-R or a functional equivalent. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA that can encode a rhMC-4R. It is well within the skilled artisan to determine an appropriate vector for a particular gene transfer or other use.

To this end, the invention also includes vectors containing an rhMC-4R gene, host cells containing the vectors, and methods of making substantially pure rhMC-R protein comprising the steps of introducing the rhMC-R gene into a host cell, and cultivating the host cell under appropriate conditions such that rhMC-R is produced. The rhMC-4R so produced may be harvested from the host cells in conventional ways. Therefore, the present invention also relates to methods of expressing the rhesus MC-4R protein and biological equivalents disclosed herein, assays employing these gene products, recombinant host cells which comprise DNA constructs which express these receptor proteins, and compounds identified through these assays which act as agonists or antagonists of MC-4R activity.

The cloned rhesus MC-4R cDNA obtained through the methods described above may be recombinantly expressed by molecular cloning into an expression vector (such as pcDNA3.neo, pcDNA3.1, pCR2.1, pCI-neo, pBlueBacHis2 or pLITMUS28) containing a suitable promoter and other appropriate transcription regulatory elements, and transferred into prokaryotic or eukaryotic host cells to produce recombinant rhesus MC-4R. Techniques for such manipulations can be found described in Sambrook, et al., supra, are discussed at length in the Example section and are well known and easily available to the artisan of ordinary skill in the art.

A variety of mammalian expression vectors may be used to express recombinant rhesus MC-4R in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. Commercially available mammalian expression vectors which may be suitable for recombinant rhesus MC-4R expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

Also, a variety of bacterial expression vectors may be used to express recombinant rhesus MC-4R in bacterial cells. Commercially available bacterial expression vectors which may be suitable for recombinant rhesus MC-4R expression include, but are not limited to pCR2.1 (Invitrogen), pET11a (Novagen), lambda gt11 (Invitrogen), and pKK223-3 (Pharmacia).

In addition, a variety of fungal cell expression vectors may be used to express recombinant rhesus MC-4R in fungal cells. Commercially available fungal cell expression vectors which may be suitable for recombinant rhesus MC-4R expression include but are not limited to pYES2 (Invitrogen) and Pichia expression vector (Invitrogen).

Also, a variety of insect cell expression vectors may be used to express recombinant receptor in insect cells. Commercially available insect cell expression vectors which may be suitable for recombinant expression of rhesus MC-4R include but are not limited to pBlueBacIII and pBlueBacHis2 (Invitrogen), and pAcG2T (Pharmingen).

Expression of rhesus MC-4R DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the rhesus MC-4R cDNA sequence(s) that yields optimal levels of rhesus MC-4R, cDNA molecules including but not limited to the following can be constructed: a cDNA fragment containing the full-length open reading frame for rhesus MC-4R as well as various constructs containing portions of the cDNA encoding only specific domains of the protein or rearranged domains of the protein. All constructs can be designed to contain none, all or portions of the 5' and/or 3' untranslated region of a rhesus MC-4R cDNA. The expression levels and activity of rhesus MC-4R can be determined following the introduction, both singly and in combination, of these constructs into appropriate host cells. Following determination of the rhesus MC-4R cDNA cassette yielding optimal expression in transient assays, this MC-4R cDNA construct is transferred to a variety of expression vectors (including recombinant viruses), including but not limited to those for mammalian cells, plant cells, insect cells, oocytes, bacteria, and yeast cells.

Therefore, another aspect of the present invention includes host cells that have been engineered to contain and/or express DNA sequences encoding the rhMC-4R. Such recombinant host cells can be cultured under suitable conditions to produce rhMC-4R or a biologically equivalent form. Recombinant host cells may be prokaryotic or eukaryotic, including but not limited to, bacteria such as *E. coli*, fungal cells such as yeast, mammalian cells including, but not limited to, cell lines of human, bovine, porcine, monkey and rodent origin, and insect cells including but not limited to *Drosophila* and silkworm derived cell lines. Therefore, an expression vector containing DNA encoding a rhesus MC-4R-like protein may be used for expression of rhesus MC-4R in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to *Drosophila*- and silkworm-derived cell lines. For instance, one insect expression system utilizes *Spodoptera frugiperda* (Sf21) insect cells (Invitrogen) in tandem with a baculovirus expression vector (pAcG2T, Pharmingen). Also, mammalian species which may be suitable and which are commercially available, include but are not limited to, L cells L-M(TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

Following expression of MC-4R in a host cell, MC-4R protein may be recovered to provide MC-4R protein in active form. Several MC-4R protein purification procedures are available and suitable for use. Recombinant MC-4R protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant MC-4R protein can be separated from other cellular proteins by use of an immunoaffinity column made with monoclonal or polyclonal antibodies specific for full-length MC-4R protein, or polypeptide fragments of MC-4R protein.

The assays described herein as well as protein purification schemes can be carried out with cells that have been transiently or stably transfected or transformed with an expression vector which directs expression of MC-4R. The expression vector may be introduced into host cells via any one of a number of techniques including but not limited to transformation, transfection, protoplast fusion, and electroporation. Transformation is meant to encompass a genetic change to the target cell resulting from an incorporation of DNA. Transfection is meant to include any method known in the art for introducing MC-4R into the test cells. For example, transfection includes calcium phosphate or calcium chloride mediated transfection, lipofection, infection with a retroviral construct containing MC-4R, and electroporation. The expression vector-containing cells are individually analyzed to determine whether they produce human MC-4R protein. Identification of human MC-4R expressing cells may be done by several means, including but not limited to immunological reactivity with anti-human MC-4R antibodies, labeled ligand binding and the presence of host cell-associated human MC-4R activity.

The specificity of binding of compounds showing affinity for rhMC-4R is shown by measuring the affinity of the compounds for recombinant cells expressing the cloned receptor or for membranes from these cells. Expression of the cloned receptor and screening for compounds that bind to rhMC-4R or that inhibit the binding of a known, radiolabeled ligand of rhMC-4R to these cells, or membranes prepared from these cells, provides an effective method for the rapid selection of compounds with high affinity for rhMC-4R. Such ligands need not necessarily be radiolabeled but can also be nonisotopic compounds that can be used to displace bound radiolabeled compounds or that can be used as activators in functional assays. Compounds identified by the above method are likely to be agonists or antagonists of rhMC-4R and may be peptides, proteins, or non-proteinaceous organic molecules.

Accordingly, the present invention is directed to methods for screening for compounds which modulate the expression of DNA or RNA encoding a MC-4R protein as well as compounds which bind to the MC-4R receptor and which may modulate MC-4R function. Methods for identifying agonists and antagonists of other receptors are well known in the art and can be adapted to identify agonists and antagonists of MC-4R. For example, Cascieri et al. (1992, *Molec. Pharmacol.* 41:1096–1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor. Where binding of the substance such as an agonist or antagonist to MC-4R is measured, such binding can be measured by employing a labeled substance or agonist. The substance or agonist can be labeled in any convenient manner known to the art, e.g., radioactively, fluorescently, enzymatically.

Therefore, the specificity of binding of compounds having affinity for MC-4R is shown by measuring the affinity of the compounds for recombinant cells expressing the cloned receptor or for membranes from these cells. Expression of the cloned receptor and screening for compounds that bind to MC-4R or that inhibit the binding of a known, radiolabeled ligand of MC-4R to these cells, or membranes prepared from these cells, provides an effective method for the rapid selection of compounds with high affinity for MC-4R. Such ligands need not necessarily be radiolabeled but can also be nonisotopic compounds that can be used to displace bound radiolabeled compounds or that can be used as activators in functional assays. Compounds identified by the above method are likely to be agonists or antagonists of MC-4R and may be peptides, proteins, or non-proteinaceous organic molecules. Compounds may modulate by increasing or attenuating the expression of DNA or RNA encoding MC-4R, or by acting as an agonist or antagonist of the MC-4R receptor protein. These compounds that modulate the expression of DNA or RNA encoding MC-4R or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing MC-4R, antibodies to MC-4R, or modified MC-4R may be prepared by known methods for such uses.

Therefore, the present invention relates to methods of expressing rhMC-4R in recombinant systems and of identifying agonists and antagonists of rhMC-4R. When screening compounds in order to identify potential pharmaceuticals that specifically interact with a target receptor, it is necessary to ensure that the compounds identified are as specific as possible for the target receptor. To do this, it is necessary to screen the compounds against as wide an array as possible of receptors that are similar to the target receptor. Thus, in order to find compounds that are potential pharmaceuticals that interact with receptor A, it is necessary not only to ensure that the compounds interact with receptor A (the "plus target") and produce the desired pharmacological effect through receptor A, it is also necessary to determine that the compounds do not interact with receptors B, C, D, etc. (the "minus targets"). In general, as part of a screening program, it is important to have as many minus targets as possible (see Hodgson, 1992, *Bio/Technology* 10:973–980, @ 980). Rhesus MC-4R proteins and the DNA molecules encoding this receptor protein have the additional utility in that they can be used as "minus targets" in screens designed to identify compounds that specifically interact with other G-protein coupled receptors. Due to homology to GPCRs, the rhMC-4R of this invention is believed to function similarly to GPCRs and have similar biological activity. They are useful in understanding the biological and physiological effects in the rhesus to in identify melanocortin active process in primates, followed by human clinical trials. More notable, rhMC-4R agonists will be identified and evaluated for their effects on food intake, weight gain, and metabolic rate to identify novel-anti-obesity agents that are effective in primates. They may also be used to scan for rhesus monkey melanocortin agonists and antagonists; as in particular to test the specificity of identified ligands.

To this end, the present invention relates in part to methods of identifying a substance which modulates MC-4R receptor activity, which involves:

(a) combining a test substance in the presence and absence of a MC-4R receptor protein wherein said MC-4R receptor protein comprises the amino acid sequence as set forth in SEQ ID NO:2; and, (b) measuring and comparing the effect of the test substance in the presence and absence of the MC-4R receptor protein.

In addition, several specific embodiments are disclosed herein to show the diverse type of screening or selection assay which the skilled artisan may utilize in tandem with an expression vector directing the expression of the MC-4R receptor protein. As noted above, methods for identifying agonists and antagonists of other receptors are well known in the art and can be adapted to identify agonists and antagonists of MC-4R. Therefore, these embodiments are presented as examples and not as limitations. To this end, the present invention includes assays by which MC-4R modulators (such as agonists and antagonists) may be identified. Accordingly, the present invention includes a method for determining whether a substance is a potential agonist or antagonist of MC-4R that comprises:

(a) transfecting or transforming cells with an expression vector that directs expression of MC-4R in the cells, resulting in test cells;

(b) allowing the test cells to grow for a time sufficient to allow MC-4R to be expressed;

(c) exposing the cells to a labeled ligand of MC-4R in the presence and in the absence of the substance;

(d) measuring the binding of the labeled ligand to MC-4R; where if the amount of binding of the labeled ligand is less in the presence of the substance than in the absence of the substance, then the substance is a potential agonist or antagonist of MC-4R.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells may be harvested and resuspended in the presence of the substance and the labeled ligand. In a modification of the above-described method, step (c) is modified in that the cells are not harvested and resuspended but rather the radioactively labeled known agonist and the substance are contacted with the cells while the cells are attached to a substratum, e.g., tissue culture plates.

The present invention also includes a method for determining whether a substance is capable of binding to MC-4R, i.e., whether the substance is a potential agonist or an antagonist of MC-4R, where the method comprises:

(a) transfecting or transforming cells with an expression vector that directs the expression of MC-4R in the cells, resulting in test cells;

(b) exposing the test cells to the substance;

(c) measuring the amount of binding of the substance to MC-4R;

(d) comparing the amount of binding of the substance to MC-4R in the test cells with the amount of binding of the substance to control cells that have not been transfected with MC-4R;

wherein if the amount of binding of the substance is greater in the test cells as compared to the control cells, the substance is capable of binding to MC-4R. Determining whether the substance is actually an agonist or antagonist can then be accomplished by the use of functional assays such as, e.g., the assay involving the use of promiscuous G-proteins described below.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells are harvested and resuspended in the presence of the substance.

Chen et al. (1995, *Analytical Biochemistry* 226: 349–354) describe a colorometric assay which utilizes a recombinant cell transfected with an expression vector encoding a G-protein coupled receptor with a second expression vector containing a promoter with a cAMP responsive element fused to the LacZ gene. Activity of the overexpressed G-protein coupled receptor is measured as the expression and OD measurement of β-Gal. Therefore, another aspect of this portion of the invention includes a non-radioactive method for determining whether a substance is a potential agonist or antagonist of MC-4R that comprises:

(a) transfecting or transforming cells with an expression vector encoding MC-4R, resulting in test cells;

(b) transfecting or transforming the test cells of step (a) with an expression vector which comprises a cAMP-inducible promoter fused to a colorometric gene such a LacZ;

(c) allowing the transfected cells to grow for a time sufficient to allow MC-4R to be expressed;

(d) harvesting the transfected cells and resuspending the cells in the presence of a known agonist of MC-4R and/or in both the presence and absence of the test compound;

(e) measuring the binding of the known agonist and test compound to overexpressed MC-4R by a colorometric assay which measures expression off the cAMP-inducible promoter and comparing expression levels in the presence of the known agonist as well as in the presence and absence of the unknown substance so as to determine whether the unknown substance acts as either a potential agonist or antagonist of MC-4R.

Additional methods of identifying agonists or antagonists include but are by no means limited to the following:

I. (a) transfecting or transforming cells with a first expression vector which directs expression of MC-4R and a second expression vector which directs the expression of a promiscuous G-protein, resulting in test cells;

(b) exposing the test cells to a substance that is a suspected agonist of MC-4R;

(c) measuring the level of inositol phosphates in the cells; where an increase in the level of inositol phosphates in the cells as compared to the level of inositol phosphates in the cells in the absence of the suspected agonist indicates that the substance is an agonist of MC-4R.

II. (a) transfecting or transforming cells with a first expression vector which directs expression of MC-4R and a second expression vector which directs the expression of a promiscuous G-protein, resulting in test cells;

(b) exposing the test cells to a substance that is an agonist of MC-4R;

(c) subsequently or concurrently to step (b), exposing the test cells to a substance that is a suspected antagonist of MC-4R;

(d) measuring the level of inositol phosphates in the cells; where a decrease in the level of inositol phosphates in the cells in the presence of the suspected antagonist as compared to the level of inositol phosphates in the cells in the absence of the suspected antagonist indicates that the substance is an antagonist of MC-4R.

III. the method of II wherein the first and second expression vectors of step (a) are replaced with a single expression vector which expresses a chimeric MC-4R protein fused at its C-terminus to a promiscuous G-protein.

The above-described methods can be modified in that, rather than exposing the test cells to the substance, membranes can be prepared from the test cells and those membranes can be exposed to the substance. Such a modification utilizing membranes rather than cells is well known in the art and is described in, e.g., Hess et al., 1992, *Biochem. Biophys. Res. Comm.* 184:260–268. Accordingly, another embodiment of the present invention includes a method for determining whether a substance binds and/or is a potential agonist or antagonist of MC-4R wherein membrane preparations from the test cells are utilized in place of the test cells. Such methods comprise the following and may utilized the physiological conditions as noted above:

(a) transfecting or transforming cells with an expression vector that directs the expression of MC-4R in the cells, resulting in test cells;

(b) preparing membranes containing MC-4R from the test cells and exposing the membranes to a ligand of MC-4R under conditions such that the ligand binds to the MC-4R in the membranes;

(c) subsequently or concurrently to step (b), exposing the membranes from the test cells to a substance;

(d) measuring the amount of binding of the ligand to the MC-4R in the membranes in the presence and the absence of the substance;

(e) comparing the amount of binding of the ligand to MC-4R in the membranes in the presence and the absence of the substance where a decrease in the amount of binding of the ligand to MC-4R in the membranes in the presence of the substance indicates that the substance is capable of binding to MC-4R.

The present invention also relates to a method for determining whether a substance is capable of binding to MC-4R comprising:

(a) transfecting or transforming cells with an expression vector that directs the expression of MC-4R in the cells, resulting in test cells;

(b) preparing membranes containing MC-4R from the test cells and exposing the membranes from the test cells to the substance;

(c) measuring the amount of binding of the substance to the MC-4R in the membranes from the test cells;

(d) comparing the amount of binding of the substance to MC-4R in the membranes from the test cells with the amount of binding of the substance to membranes from control cells that have not been transfected with MC-4R, where if the amount of binding of the substance to MC-4R in the membranes from the test cells is greater than the amount of binding of the substance to the membranes from the control cells, then the substance is capable of binding to MC-4R.

A preferred embodiment of the present invention is determining various ligand binding affinities using $^{125}$I-labeled NDP-α-MSH as the labeled ligand in the presence of varying concentration of unlabeled ligands. The activation of the second messenger pathway may be determined by measuring the intracellular cAMP elicited by agonist at various concentration.

The present invention also relates to polyclonal and monoclonal antibodies raised in response to either the rhesus form of MC-4R, or a biologically active fragment thereof.

Polyclonal or monoclonal antibodies may be raised against rhesus MC-4R or a synthetic peptide (usually from about 9 to about 25 amino acids in length) from a portion of rhesus MC-4R as disclosed in SEQ ID NO:2. Monospecific antibodies to rhesus MC-4R are purified from mammalian antisera containing antibodies reactive against rhesus MC-4R or are prepared as monoclonal antibodies reactive with rhesus MC-4R using the technique of Kohler and Milstein (1975, Nature 256: 495–497). Monospecific antibody as used herein is defined as a single antibody species or multiple antibody species with homogenous binding characteristics for rhesus MC-4R. Homogenous binding as used herein refers to the ability of the antibody species to bind to a specific antigen or epitope, such as those associated with rhesus MC-4R, as described above. Rhesus MC-4R-specific antibodies are raised by immunizing animals such as mice, rats, guinea pigs, rabbits, goats, horses and the like, with an appropriate concentration of rhesus MC-4R protein or a synthetic peptide generated from a portion of rhesus MC-4R with or without an immune adjuvant.

Preimmune serum is collected prior to the first immunization. Each animal receives between about 0.1 μg and about 1000 μg of rhesus MC-4R protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of rhesus MC-4R protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of rhesus MC-4R in Freunds incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with rhesus MC-4R are prepared by immunizing inbred mice, preferably Balb/c, with rhesus MC-4R protein. The mice are immunized by the IP or SC route with about 1 μg to about 100 μg, preferably about 10 μg, of rhesus MC-4R protein in about 0.5 ml buffer or saline incorporated in an equal volume of an acceptable adjuvant, as discussed above. Freunds complete adjuvant is preferred. The mice receive an initial immunization on day 0 and are rested for about 3 to about 30 weeks. Immunized mice are given one or more booster immunizations of about 1 to about 100 μg of rhesus MC-4R in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using rhesus MC-4R as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-rhesus MC-4R mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of rhesus MC-4R in body fluids or tissue and cell extracts.

It is readily apparent to those skilled in the art that the above described methods for producing monospecific antibodies may be utilized to produce antibodies specific for rhesus MC-4R peptide fragments, or full-length rhesus MC-4R.

Rhesus MC-4R antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length rhesus MC-4R or rhesus MC-4R protein fragments are slowly passed through the column. The column is then washed with phosphate buffered saline until the optical density ($A_{280}$) falls to background, then the protein is eluted with 0.23 M glycine-HCl (pH 2.6). The purified rhesus MC-4R protein is then dialyzed against phosphate buffered saline.

The specificity of binding of compounds showing affinity for rhMC-4R is shown by measuring the affinity of the compounds for recombinant cells expressing the cloned receptor or for membranes from these cells. Expression of the cloned receptor and screening for compounds that bind to rhMC-4R or that inhibit the binding of a known, radiolabeled ligand of rhMC-4R to these cells, or membranes prepared from these cells, provides an effective method for the rapid selection of compounds with high affinity for rhMC-4R. Such ligands need not necessarily be radiolabeled but can also be nonisotopic compounds that can be used to displace bound radiolabeled compounds or that can be used as activators in functional assays. Compounds identified by the above method are likely to be agonists or antagonists of rhMC-R and may be peptides, proteins, or non-proteinaceous organic molecules.

The DNA molecules, RNA molecules, recombinant protein and antibodies of the present invention may be used to screen and measure levels of rhesus MC-4R. The recombinant proteins, DNA molecules, RNA molecules and antibodies lend themselves to the formulation of kits suitable for the detection and typing of rhesus MC-4R. Such a kit would comprise a compartmentalized carrier suitable to hold in close confinement at least one container. The carrier would further comprise reagents such as recombinant MC-4R or anti-MC-4R antibodies suitable for detecting rhesus MC-4R. The carrier may also contain a means for detection such as labeled antigen or enzyme substrates or the like.

Pharmaceutically useful compositions comprising modulators of rhesus MC-4R may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified rhesus MC-4R, or either MC-4R agonists or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individuals condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drugs availability to target sites. This involves a consideration of the distribution, equilibrium, and elimination of a drug.

The following examples are provided to illustrate the present invention without, however, limiting the same hereto.

EXAMPLE 1

Isolation of the Rhesus MC-4R Gene

A series of oligonucleotides were designed to isolate the full length MC-4R genes based on the human MC-4R gene sequence. These oligonucleotides were designed to incorporate a restriction enzyme site for cloning into the expression vector pCI-neo (Promega). The following oligos were used:

```
rhMRC4F1 5'CCGGCTCGAGGAATTCTCCTGCCAGCATG-3'      (SEQ ID NO:3)

rhMCR4F2 5'CCGGCTCGAGCCTGCCAGCATGGTGAA-3'       (SEQ ID NO:4)

rhMCR4R1 5'CCGGTCTAGACGTGCTCTGTCCCCATTTA-3'     (SEQ ID NO:5)

rhMCR4R2 5'CCGGTCTAGAGTCCCCATTTAATATCTGCTAGA-3' (SEQ ID NO:6)
```

PCR reactions were performed in a 500 µl eppendorf tube under mineral oil in 50 µl volumes using Taq Polymerase (Gibco/BRL) which included the following: 1×Taq buffer (Gibco/BRL), 0.3 mM dGTP, 0.3 mM dCTP, 0.3 mM dATP, 0.3 mM dGTP, 100 ng rhesus genomic DNA (Clontech), 20 pM of each primer, and 2 mM MgCl2, and 2 Units of Taq Polymerase. Reactions were set up initially lacking Taq Polymerase and performed in a Omnigene thermal cycler (Hybraid) under the following conditions: 94° C. for 60 sec, 60° C. for 20 sec, then held at 60° C. until Taq Polymerase was added, then 72° C. for 120 sec, then 35 cycles of 94° C. for 20 sec, 60° C. for 20 sec, and 72° C. for 110 sec. The final cycle was an additional 8 min at 72° C. and 10 min at 30° C. In the initial experiments, no bands were visible after running 1/10 of the PCR products on a 1% agarose gel. After increasing the time for the 72° C. elongation step to 130 sec products were obtained of the predicted size (about 1.0 kb) using the four combinations of rhMCR4 primers. The products of the rhMRC4F1 and rhMCR4R1 primers was purified away from contaminating reaction products using a QIAquick PCR Purification kit (Qiagen), and digested with a mixture of EcoRI and XbaI restriction enzymes which were used according to the manufactures directions (Gibco/BRL). The pCI-neo vector DNA was also cleaved with EcoRI and XbaI. Both the vector and PCR products were purified on a 1% agarose gel, the approximately 1.0 kb PCR product band and the 5.5 kb vector bands were excised from the gel, and the DNA purified from the gel with a QIAquick Gel Extraction kit (Qiagen). The vector and PCR fragments were ligated in a 1:3 ratio using T4 DNA ligase (Gibco/BRL). The resulting plasmids were transformed into DH5a cells (Library efficiency grade, Gibco/BRL), and after 1 hr of expression, plated on LB agar plates (Digene) with 100 µg/ml ampicillin (Sigma). After 24 hrs colonies were picked, grown overnight at 37° C. in 1 ml cultures of Superbroth (Digene), and DNA prepared for Sequencing using the QIAwell Ultra kit (Qiagen). DNA cycle sequencing was performed on four independent PCR products using a Prism kit (Applied Biosytems), the reaction products run on an ABI 373A DNA sequencer, and the resulting data analyzed using Sequencher (Gene Codes). Sequencing confirmed that the pVE3099 encoded a GPCR with high homology to the human MC-4R receptor. The rhMC-4R receptor gene encoded by pVE3099 is 98% identical to the human receptor gene and the rhMC-4R receptor is also 98% identical at the amino acid level to the human MC-4R receptor.

EXAMPLE 2

Transient Expression of Rhesus MC-4R

Four 800 ml triple flasks (Nalge Nunc) containing 125 ml of Dulbecco's modified Eagle Medium (DMEM), Gibco-BRL) supplemented with 10% fetal bovine serum (Sigma), L-glutamine (Gibco/BRL), and Pen/Strep (Gibco/BRL) were inoculated with COS 7 cells, and incubated for 4 days. The cells in each flask were collected by pouring off the media, adding 30 ml of trypsin/EDTA (0.05%, Gibco/BRL) to each flask and letting the flasks incubate at room temp for 2 min. Then the tyrpsin solution was removed, and the flasks incubated at 37° C. for 10 minutes, 30 ml of DMEM added, and the cells collected. The cells were pelleted at 1000 rpm for 8 min., washed twice with Delbecco's PBS lacking $Mg^{++}$ and $Ca^{++}$ (Gibco/BRL). The cells were counted and resuspended to a density of $1.2 \times 10^7$/ml of PBS lacking $Mg^{++}$ and $Ca^{++}$. DNA was introduced into the cells by electroporation; 0.85 ml of cells was mixed with 20 µg of pVE3099, the rhMCR4 expressing clone, in an ice cold 0.4 cm cuvette (BioRad). The solution was electroporated with a BioRad Gene Pulsar elctroporator set to 0.26 kV, 960 µFD. The cells from 30 electroporations were pooled into 1 liter of DMEM and dispensed 125 ml per triple flask and incubated at 37° C.

Three days later the media from each flask was poured off, the cells were washed with 100 ml of Delbecco's PBS lacking $Mg^{++}$ and $Ca^{++}$, and 30 ml of enzyme-free dissociation buffer (Gibco/BRL) added. After incubation at room temperature for 10 min., cells were collected, centrifuged at 1000 rpm for 10 min. at 4° C., and resuspended into 15 ml of membrane buffer (10 mM Tris pH 7.4, with proteinase inhibitors). A 500× proteinase inhibitor solution contains Leupeptin (Sigma) 2 mg/ml, Phosphoramidon (Sigma) 5 mM, Bacitracin (Sigma) 20 mg/ml, Aprotinin (Sigma) 2.5 mg/ml, and 0.05 M AEBSF (Pefabloc). Cells are disrupted with 10 strokes of a motor driven dounce, the homogenate transferred to 50 ml Falcon tubes and spun at 2200 rpm, 4° C. for 10 min. The supernatant was transferred to 50 ml centrifuge tubes and spun at 18K for 20 min. in a Sorvall RC5B centrifuge. The membranes were resuspended into 0.6 ml of membrane buffer, passed 2 times through a 18 gauge needle and 5 times through a 25 guage needle, aliquoted, frozen in liquid nitrogen, and stored at −80° C. until needed.

EXAMPLE 3

Stable Expression of Rhesus MC-4R

Chinese Hamster Ovary (CHO) cells were plated into 6 well tissue culture dishes in complete media (ISCOVEís DMEM with the following supplements: 10% FBS, antibiotics, 2 mM glutamine, 0.1 mM sodium hypoxanthine, 0.016 mM thymidine (Gibco BRL)) so that 2 days post-plating they were at roughly 50% confluence. For each well, the rhesus MC-4R receptor gene (2 ug) was added to 50 µl of ISCOVE's DMEM (no supplements) and 5 µl SuperFect reagent (Qiagen) in a sterile tube, gently mixed and allowed to incubate at room temperature for 10 minutes. During the last minute of incubation, the media was removed from the cells and the monolayers were rinsed with PBS and removed. At the end of the 10 minute incubation, 0.35 mls of complete media was added to the DNA mixture and added dropwise to the cells. The cells were incubated with the DNA solution in a 37° C. $CO_2$ incubator for 2–4 hrs. At the end of the 37° C. incubation, the DNA solution was removed, cells were rinsed 1× with PBS, and then fed with complete media. The next day the cells were detached with Trypsin and replated in complete media containing 1 mg/ml Geneticin (Gibco BRL). After 7–14 days Geneticin-resistant clones were identified and isolated. Clones demonstrating specific binding of $^{125}$I-NDP-alpha-MSH were selected.

EXAMPLE 4

Pharmacological Properties of Rhesus MC-4R

Competitive Binding Assays—Binding reactions (total volume=250 µl) contained MBB (50 mM Tris pH 7.2, 2 mM $CaCl_2$, 1 mM $MgCl_2$), 0.1% BSA, crude membranes prepared from cells expressing human MC3, MC4 or MC5 receptor, 200 pM [$^{125}$I]-NDP alpha MSH (Amersham Corp.), and increasing concentrations of unlabelled test compounds dissolved in DMSO (DMSO final concentration=2%). Reactions were incubated for 1 hour without shaking and then filtered through 96-well filter plates (Packard corp.). Filters were washed three times with TNE buffer (50 mM Tris pH 7.4, 5 mM EDTA, 150 mM NaCl), dried and counted using Microscint-20 in a Topcount scintillation counter (Packard). Non-specific binding was determined in the presence of 2 µM unlabelled NDP alpha MSH (Peninsula laboratories).

Membranes prepared from rhesus MC-4R transfected cells were evaluated alongside membranes prepared from human MC-4R, MC-4R, and MC-5R expressing cells. The data in Table 1 represents the average of 2 independent determinations. Human and rhesus MC-4R showed similar rank-order potencies for the natural ligands ACTH>alpha MSH=beta MSH>gamma MSH. The ligands alpha and gamma MSH show greater relative differences in affinity for the rhesus MC-4 receptor compared to human MC-4R.

TABLE 1

Pharmacology of Melanocortin Peptides at the Rhesus MC-4 Receptor.

| Ligand | IC50 in nM | | | |
|---|---|---|---|---|
| | hMC-3R | hMC-4R | rhMC-4R | hMC-5R |
| Alpha MSH | 13 | 10 | 27 | 157 |
| Beta MSH | 23 | 12 | 23 | 166 |
| Gamma MSH | 75 | 761 | 211 | 2800 |
| ACTH1-39 | 6 | 6 | 1.3 | 0.4 |
| NDP-alpha-MSH | 0.6 | 0.6 | 1.3 | 0.4 |
| MTII | 1.6 | 0.1 | 0.1 | 0.9 |
| SHU-9119 | 0.3 | 0.1 | 0.2 | 0.1 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

The invention claimed is:

1. A method for determining whether a substance is capable of activating rhMC-4R comprising:
   (a) providing test cells by transfecting cells with an expression vector that directs the expression of rhMC-4R in the cells, said expression vector comprising a nucleic acid that encodes the amino acid sequence as set forth in SEQ ID NO:2;
   (b) exposing the test cells to the substance;
   (c) measuring the amount of accumulated intracellular cAMP; and,
   (d) comparing the amount of cAMP in the test cells in response to the substance with the amount of cAMP in test cells that have not been exposed to the substance; wherein an increase in the amount of cAMP in test cells in response to the substance indicates that the substance is capable of activating rhMC-4R.

2. A method of identifying agonists of MC-4R comprising:
   (a) transfecting or transforming cells with a first expression vector which directs expression of a rhesus monkey MC-4R and a second expression vector which directs the expression of a promiscuous G-protein, resulting in test cells, said first expression vector comprising a DNA molecule that encodes the amino acid sequence as set forth in SEQ ID NO:2;
   (b) exposing the test cells to a substance that is a suspected agonist of MC-4R; and,
   (c) measuring the level of inositol phosphate in the cells; where an increase in the level of inositol phosphate in the cells as compared to the level of inositol phosphate in the cells in the absence of the suspected agonist indicates that the substance is an agonist of MC-4R.

3. A method of identifying antagonists of MC-4R comprising:
   (a) transfecting or transforming cells with a first expression vector which directs expression of a rhesus monkey MC-4R and a second expression vector which directs the expression of a promiscuous G-protein, resulting in test cells, said first expression vector comprising a DNA molecule that encodes the amino acid sequence as set forth in SEQ ID NO:2;
   (b) exposing the test cells to a substance that is an agonist of MC-4R;
   (c) subsequently or concurrently to step (b), exposing the test cells to a substance that is a suspected antagonist of MC-4R; and,
   (d) measuring the level of inositol phosphate in the cells; where a decrease in the level of inositol phosphate in the cells in the presence of the suspected antagonist as compared to the level of inositol phosphate in the cells in the absence of the suspected antagonist indicates that the substance is an antagonist of MC-4R.

4. A method of identifying antagonists of MC-4R as recited in claim 3 wherein the first and second expression vectors of step (a) are replaced with a single expression vector which expresses a chimeric MC-4R protein fused at its C-terminus to a promiscuous G-protein.

* * * * *

SEQUENCE LISTING

<160> NUMBER OF SEQ ID NOS: 6

<210> SEQ ID NO 1
<211> LENGTH: 1030
<212> TYPE: DNA
<213> ORGANISM: rhesus monkey (Macaca mulatta)

<400> SEQUENCE: 1

```
gaattctcct gccagcatgg tgaactccac ccaccgtggg atgcacgctt ctctgcacct      60
ctggaaccgc agcagccaca gactgcacag caatgccagt gagtcccttg gaaaaggcta     120
ctctgatgga gggtgctacg agcaactttt tgtctctcct gaggtgtttg tgacactggg     180
tgtcatcagc ttgttggaga atatcttagt gattgtggca atagccaaga acaagaatct     240
gcattcaccc atgtactttt tcatctgcag cctggctgtg gctgatatgc tggtgagcgt     300
ttcaaatgga tcagaaacca ttgtcatcac cctattaaac agtacagata cggacacaca     360
gagtttcaca gtgaacattg ataatgttat tgactcagtg atctgtagct ccttgcttgc     420
atccatttgc agcctgcttt caattgcagt ggacaggtac tttactatct tctatgctct     480
tcagtaccat aacattatga cagttaagcg ggttgggatc atcataagtt gtatctgggc     540
agcttgcacg gtttcaggca ttttgttcat catttactca gatagtagtg ctgtcatcat     600
ctgcctcatc accatgttct tcaccatgtt ggctctcatg gcttctctct atgtccacat     660
gttcctgatg gccaggcttc acattaagag gattgctgtc ctccccggca ctggtgccat     720
ccgccaaggc gccaatatga agggagcgat tactttgacc atcctgattg gcgtcttttgt     780 tgtctgctgg gcccccattct tcctccactt aatattctac atctcttgtc ctcagaatcc     840
atattgtgtg tgcttcatgt ctcactttaa cttgtatctc atactgatca tgtgtaattc     900
agtcatcgat cctctgattt atgcactccg gagtcaagaa ctaaggaaaa ccttcaaaga     960
gatcatctgt tgctatcccc tgggaggcct atgtgacttg tctagcagat attaaatggg    1020
gacagagcac                                                            1030
```

<210> SEQ ID NO 2
<211> LENGTH: 332
<212> TYPE: PRT
<213> ORGANISM: rhesus monkey (Macaca mulatta)

<400> SEQUENCE: 2

Met Val Asn Ser Thr His Arg Gly Met His Ala Ser Leu His Leu Trp
1               5                   10                  15

Asn Arg Ser Ser His Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Thr Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Val Ile Asp Pro Leu Ile Tyr Ala Leu
    290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 3
<211> LENGTH: 29
<212> TYPE: DNA
<213> ORGANISM: Artificial Sequence
<220> FEATURE:
<223> OTHER INFORMATION: OLIGONUCLEOTIDE

<400> SEQUENCE: 3

```
                                    -continued ccggctcgag gaattctcct gccagcatg                                  29

<210> SEQ ID NO 4
<211> LENGTH: 27
<212> TYPE: DNA
<213> ORGANISM: Artificial Sequence
<220> FEATURE:
<223> OTHER INFORMATION: OLIGONUCLEOTIDE

<400> SEQUENCE: 4
ccggctcgag cctgccagca tggtgaa                                    27

<210> SEQ ID NO 5
<211> LENGTH: 29
<212> TYPE: DNA
<213> ORGANISM: Artificial Sequence
<220> FEATURE:
<223> OTHER INFORMATION: OLIGONUCLEOTIDE

<400> SEQUENCE: 5
ccggtctaga cgtgctctgt ccccattta                                  29

<210> SEQ ID NO 6
<211> LENGTH: 33
<212> TYPE: DNA
<213> ORGANISM: Artificial Sequence
<220> FEATURE:
<223> OTHER INFORMATION: OLIGONUCLEOTIDE

<400> SEQUENCE: 6
ccggtctaga gtccccattt aatatctgct aga                             33
```